(12) United States Patent
Kaufmann et al.

(10) Patent No.: US 9,592,364 B2
(45) Date of Patent: Mar. 14, 2017

(54) CATHETER AND METHOD FOR PRODUCING THE SAME

(71) Applicant: VascoMed GmbH, Binzen (DE)

(72) Inventors: Ralf Kaufmann, Loerrach (DE); Siegfried Schreiber, Grenzach-Wyhlen (DE); Paul Rath-Prazak, Breisach (DE)

(73) Assignee: VascoMed GmbH, Binzen (DE)

(*) Notice: Subject to any disclaimer, the term of this patent is extended or adjusted under 35 U.S.C. 154(b) by 994 days.

(21) Appl. No.: 13/711,076

(22) Filed: Dec. 11, 2012

(65) Prior Publication Data
US 2013/0158478 A1 Jun. 20, 2013

Related U.S. Application Data

(60) Provisional application No. 61/576,364, filed on Dec. 16, 2011.

(51) Int. Cl.
| | |
|---|---|
| *A61M 25/00* | (2006.01) |
| *A61M 25/01* | (2006.01) |
| *A61B 18/14* | (2006.01) |
| *B23K 10/02* | (2006.01) |

(52) U.S. Cl.
CPC ..... *A61M 25/0147* (2013.01); *A61B 18/1492* (2013.01); *A61M 25/0009* (2013.01); *B23K 10/02* (2013.01); *A61M 2025/015* (2013.01); *Y10T 29/49002* (2015.01)

(58) Field of Classification Search
CPC .............. A61M 25/01; A61M 25/0105; A61M 25/0133; A61M 25/0147; A61M 2025/015; A61B 18/14; A61B 18/1492
USPC ............ 604/95.01, 95.04, 523, 528; 606/129
See application file for complete search history.

(56) References Cited

U.S. PATENT DOCUMENTS

| | | | | |
|---|---|---|---|---|
| 5,368,592 | A * | 11/1994 | Stern | A61M 25/0147 403/90 |
| 2001/0025134 | A1 | 9/2001 | Bon et al. | |
| 2003/0130598 | A1* | 7/2003 | Manning | A61B 5/0422 600/585 |
| 2009/0163917 | A1 | 6/2009 | Potter | |

FOREIGN PATENT DOCUMENTS

| | | |
|---|---|---|
| EP | 1 690 510 | 8/2006 |
| EP | 1 803 480 | 7/2007 |
| EP | 2275163 | 1/2011 |

OTHER PUBLICATIONS

European Search Report and Notes to the European Search Report on European Patent Application No. EP 12 19 0721, dated Feb. 12, 2013 (10 pages).

* cited by examiner

*Primary Examiner* — Aarti B Berdichevsky
(74) *Attorney, Agent, or Firm* — Buchanan Ingersoll & Rooney PC

(57) ABSTRACT

A catheter comprising a steering cable anchor, which is preferably disposed at the distal end of the catheter, and a steering cable. In order to obtain a reliable connection between the steering cable anchor and the steering cable, which is also suitable for use in MRI, a substantially dumbbell-shaped element is disposed between the steering cable anchor and the steering cable and connects the steering cable anchor to the steering cable.

10 Claims, 2 Drawing Sheets

CATHETER AND METHOD FOR PRODUCING THE SAME

CROSS-REFERENCE TO RELATED APPLICATIONS

This patent application claims the benefit of U.S. Provisional Patent Application No. 61/576,364, filed on Dec. 16, 2011, which is hereby incorporated by reference in its entirety.

TECHNICAL FIELD

The present invention relates to catheters and, in particular, to a protective sleeve for a catheter comprising a steering cable anchor, which is preferably disposed at distal ends of the catheter, and a steering cable, and also to a method for producing such a catheter.

BACKGROUND

In general, small tubes or hoses having various diameters and made of various materials, which can be used to probe, empty, fill or rinse hollow organs such as, for example, the bladder, stomach, intestine, blood vessels and/or the heart, are referred to as catheters. A special form of intravascularly used catheters, especially for applications in the heart/thorax region, are catheters comprising an electrode which are introduced into primary veins or arteries, such as the femoral vein, for example, and advanced from there to various locations of the heart or in the coronary vessels. These catheters are used to represent or stimulate the electrical activity of the heart or remove regions exhibiting abnormal electrical activity. The latter, which is referred to as ablation therapy, is used as a treatment for cardiac dysrhythmia, for example.

So as to be able to handle such a catheter, the metallic steering cable anchor, which is provided at the distal end of the catheter and designed, for example, as an electrode, is connected to a steering cable, which is typically designed as a pull wire. This steering cable is moved by a plunger, which is arranged at the proximal end of the catheter and extends from the proximal end of the catheter to the distal end. A movement of the plunger in the longitudinal direction with respect to the plunger chamber results in a curvature of the catheter in the central region.

Efforts have been ongoing for quite some time to employ the magnetic resonance imaging ("MRI") method not only as a diagnostic imaging technique, but also for monitoring the positioning and success of simultaneously conducted catheter procedures, for example, during therapeutic procedures against cardiac dysrhythmia. This necessitates catheter designs that are amagnetic and withstand the stresses of strong alternating electromagnetic fields. In such alternating fields, catheter elements must not shift nor heat up, nor perform mechanical oscillations. Moreover, no catheter-induced image artifacts must occur.

One option to protect an intravascularly used catheter system from the effects of a very strong alternating electromagnetic field is to employ non-metallic materials.

During the attempts to replace metallic elements with non-metallic elements, the observation was made that in manually steerable catheters, notably the metallic steering cable, which acts like an antenna in the alternating electric field, heats up at the ends and is thus not suitable for use in the MRI. If the steering cable is produced of non-metallic materials, especially the design of a reliable, dynamically very resilient connection system to corresponding anchors, for example, the electrode, which is preferably disposed at the distal end of the catheter, is critical for the reliable function of electrophysiological catheters.

A catheter comprising an electrode is known from the document EP 2 275 163 A2. This document describes several options for connecting a tip electrode to a puller wire made of a material such as high molecular density polyethylene. A solution that is shown and described in this document employs a pin projecting from the distal electrode transversely to the longitudinal direction, with the puller wire being wrapped around this pin and the puller wire being fixed thereto. However, the known solution consumes a lot of space because the pin projects perpendicularly to the longitudinal catheter axis. This limits the available space for the electrical and hydraulic lines in the catheter shaft. Moreover, the tensile load applied by the puller wire bends the pin. Additionally, metals are not very resistant to such bending loads, so that the known connection must be considered unreliable.

The present invention is directed toward overcoming one or more of the above-identified problems.

SUMMARY

It is thus an object of the present invention to create a catheter which can be employed in MRI and which is also reliable and dynamically very resilient. It is a further object of the present invention to provide a method for producing such a catheter, by which such a catheter is easy and cost-effective to produce.

At least the above object is achieved by the subject matter described in the independent claim(s). The catheter according to the present invention, in particular, comprises a substantially dumbbell-shaped element, which is disposed between the steering cable anchor and the steering cable and connects the electrode to the steering cable.

In the present catheter according to the present invention, the dumbbell-shaped element, which is preferably made of a metallic material, forms a component that connects the metallic steering cable anchor to the non-metallic steering cable, which is preferably made of a high-strength polymer exhibiting limited extensibility, in a simple manner. This establishes a statically and dynamically highly resilient connection, for example, between the metallic electrode acting as the tension rod, which is designed, in particular, as a distal electrode, and the steering cable, so that the electrophysiological catheter can be steered and/or bent. As an alternative or in addition, the dumbbell-shaped element may contain, for example, glass, ceramic material and/or plastic material, such as, for example, PEEK (polyether ether ketone).

Compared to the steering cable (for example, in the form of a pull wire), the dumbbell-shaped element has a short length, so that the same does not act as an antenna in the alternating electromagnetic fields that are present in the MRI, and no image artifacts develop, even if it is made of a metallic material.

At the one, proximal, end, the dumbbell-shaped element is designed so that the steering cable, which is preferably designed as a pull wire, can be rigidly and tightly attached using a knot technique. The other, distal, end of the dumbbell-shaped element can be connected to the steering cable anchor, such as the electrode, by way of soldering, welding, pressing, gluing and/or a screw connection, for example. This establishes a reliable and dynamically resilient connection between the electrode and the steering cable.

Moreover, the dumbbell-shaped element is designed such that the connecting element takes up only a small part of the catheter cross-section. This leaves plenty of room for other functional elements, such as, for example, electrical and/or hydraulic lines, and other catheter lumina. This applies notably in an arrangement of the dumbbell-shaped element such that the longitudinal axis thereof runs parallel, or substantially parallel, which is to say at a small angle, with respect to the longitudinal axis of the catheter or steering cable.

The dumbbell-shaped element preferably comprises a first end section and a second end section, as well as a center section interdisposed between them, wherein the first end section is preferably connected to the electrode, and the steering cable is attached to the second end section. This design of the dumbbell-shaped allows resilient connections to be established reliably and easily both to the electrode and to the steering cable.

As was already described above, the steering cable contains a polymer, preferably a highly crystalline, highly drawn ultra high molecular polyethylene (UHMPE), and the electrode and/or the dumbbell-shaped element contain a metallic material, wherein the dumbbell-shaped element is preferably not ferromagnetic. The dumbbell-shaped element is produced from a nickel titanium (NiTi) alloy, for example. This is particularly advantageous because NiTi is antimagnetic and has a high tensile strength. A further advantage of using NiTi is that it is corrosion-resistant and cost-effective. Such a dumbbell-shaped element can be produced by means of, for example, plasma jet welding or plasma jet melting at the ends of a corresponding wire section.

As compared to the interposed center section, the first end section and the second end section of the dumbbell-shaped element are thicker in a direction transversely to the longitudinal axis of the dumbbell-shaped element (which is to say in the radial direction), and preferably have a maximum diameter in the radial direction of the dumbbell-shaped element that is at least twice the diameter of the center section in the radial direction. This creates a good option, not only for attaching the non-metallic steering cable with the steering cable anchor to the center section in a reliable and dynamically highly resilient manner, for example, by means of a bowline knot, in the form of a loop, and a sheepshank knot that is wrapped around once or multiple times, but also for reliably connecting the dumbbell-shaped element having a large cross-section to the steering cable anchor. The advantage of using a sheepshank or bowline is that the sheepshank or bowline contracts when tensile forces occur along the steering cable.

In the region of the connection between the first end section and the steering cable, at least one groove, which particularly preferably runs parallel to the longitudinal axis of the catheter, may be provided in the dumbbell-shaped element in the first end section and/or the center section, preferably at the proximal end, the groove guiding the steering cable along the dumbbell-shaped element.

The center section of the dumbbell-shaped element preferably has a diameter of less than approximately 1 mm and a length of at least approximately 3 mm, preferably a length of at least approximately 5 mm, and still more preferably a length of no more than approximately 10 mm. Given the selected boundaries for the dimensions of the dumbbell-shaped element, the dumbbell-shaped element effects a reliable connection between the steering cable and electrode, as well as low interaction with the alternating electromagnetic fields of the MRI.

The use of a polymer, and more particularly of a highly crystalline, highly drawn UHMPE, for the steering cable is advantageous because it does not interfere with the alternating electromagnetic field and develops no antenna effect. It is further advantageous that the bending radii of polymers are much smaller in relation to the diameter. Moreover, polymers are more buckling-proof than metallic material, so that smaller deflection radii of the catheter can be implemented. This gives the catheter according to the present invention greater bending flexibility.

In a refinement of the present invention, the first end section of the dumbbell-shaped element is positively connected to the steering cable anchor and is, for example, soldered, welded and/or screwed into a corresponding recess of the steering cable anchor.

The first end section and/or the second end section of the dumbbell-shaped element are designed, for example, as spheres, spherical segments, cones, conical segments or cylinders. This design of the end section of the dumbbell-shaped element makes it particularly easy either to arrange the respective section in a corresponding recess of the steering cable anchor, or to connect the respective section to the steering cable by attaching a knot or a loop. The end section of the dumbbell-shaped element which faces the steering cable forms the stop for the knot or loop, over which the knot or loop cannot slide due to the large diameter. The steering cable is thus preferably designed as a loop at the distal end, with this loop being wrapped around the second end section of the dumbbell-shaped element. This connection between the steering cable and steering cable anchor works without the use of adhesives, which could negatively influence the properties of a polymeric steering cable, for example, by reacting therewith.

As was already described above, the longitudinal axis of the dumbbell-shaped element preferably runs parallel to the longitudinal catheter axis, whereby the forces applied by the steering cable do not cause bending of the dumbbell-shaped element and merely constitute a tensile load. This is advantageous because metals generally tolerate a higher tensile load than a bending load. The arrangement according to the present invention thus allows for high static and cyclic tensile loads to be transmitted into the distal electrode or the steering cable anchor, up to the ultimate tensile strength of the steering cable. The arrangement of the dumbbell-shaped element is thus moreover very space-saving and stable because the dumbbell leaves sufficient clearance for other signal and media lines extending to the electrode.

At least the above object is also achieved by a method for producing a catheter comprising a steering cable anchor, which is preferably disposed at the distal end of the catheter and preferably designed as an electrode, and a steering cable, comprising the steps described in claim 11. The method according to the present invention notably comprises the following steps:

a) producing a steering cable anchor and the steering cable, b) producing a dumbbell-shaped element having a first end section and a second end section and a center section interposed between them, c) connecting the steering cable anchor to the first end section of the dumbbell-shaped element, preferably by way of a positive connection, and d) connecting the steering cable to the second end section of the dumbbell-shaped element, preferably by attaching the steering cable to the second end section.

The above method according to the present invention is a simple production method, which moreover can be carried out cost-effectively and reproducibly. The steering cable is preferably fastened to the second end section of the dumbbell-shaped element by means of a loop that is wrapped around multiple times. However, other fastening methods can also be implemented.

Moreover, in a preferred exemplary embodiment, the steering cable can additionally comprise at least one groove running preferably in the longitudinal direction of the catheter for guiding the steering cable.

The production method according to the present invention can be designed particularly easily by producing the dumbbell-shaped element from a wire, and preferably from a wire made of a NiTi alloy, wherein the first end section and/or the second end section are preferably generated by means of plasma jet welding. The wire, which initially is present in the center section, is thus thickened at the end in a simple manner.

Further features, aspects, objectives, characteristics, advantages, and application options of the present invention will be apparent from the following description of one exemplary embodiment of a catheter according to the present invention based on the figures. All characteristics described and/or illustrated, either alone or in any arbitrary combination, form the subject matter of the present invention, independently of their combination in the individual claims or dependent claims.

DETAILED DESCRIPTION

Figure 1:
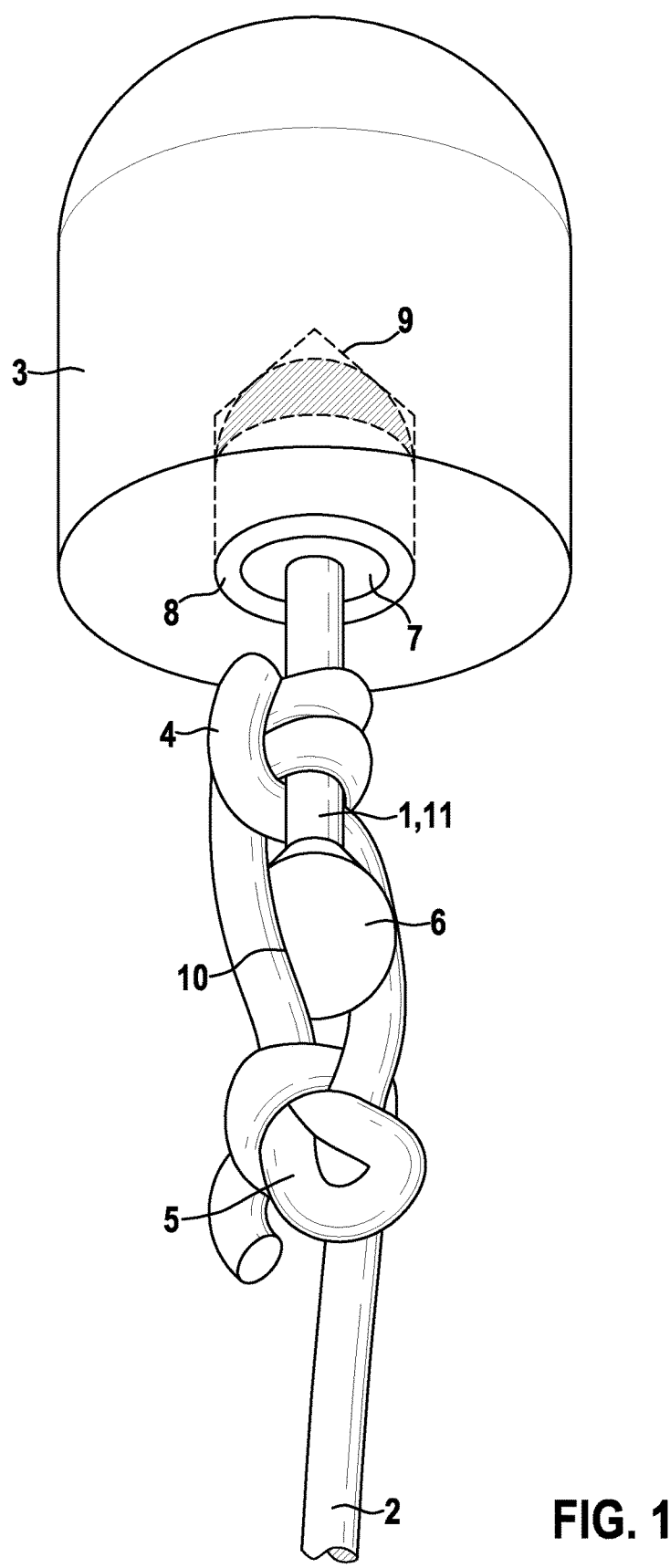
FIG. 1 is a perspective side view of the connection between a distal electrode and a pull wire of the catheter shown in FIG. 2.
Figure 2:
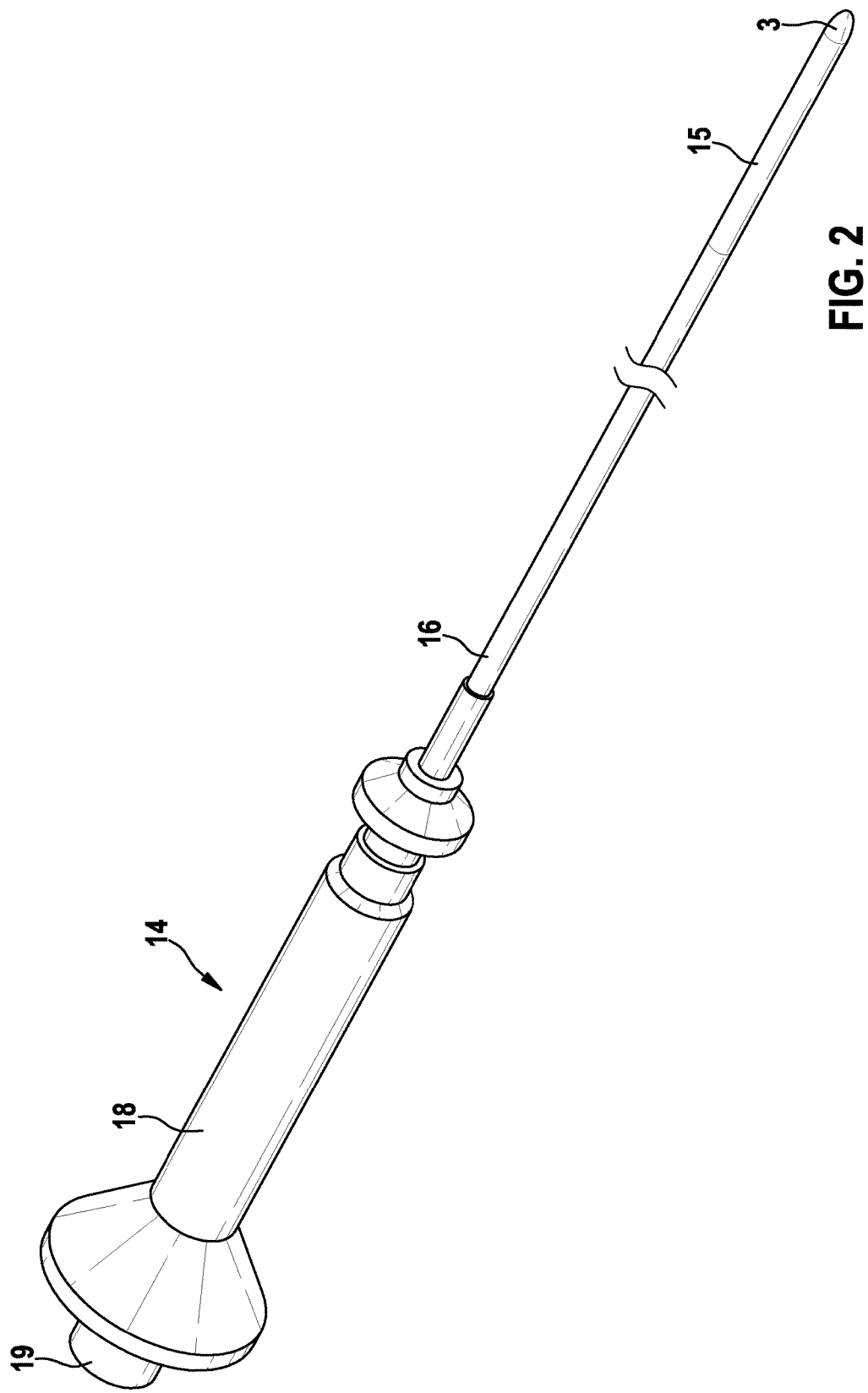
FIG. 2 is a side view of an exemplary embodiment of a catheter according to the present invention.

FIG. 1 illustrates the connection between a substantially cylindrical distal electrode 3 and a pull wire 2, as it is present according to the present invention in the catheter shown in FIG. 2.

According to the present invention, a dumbbell-shaped element 1 having a first end section 7, which in the exemplary embodiment shown as designed in the shape of a sphere, and a second end section 6, which likewise has a spherical shape, is provided between the distal electrode 3 and the pull wire 2. The center section 11, which is wire-shaped, is disposed between the first end section 7 and the second end section 6 of the dumbbell-shaped element 1. The first end section 7 is soldered into a substantially cylindrical proximal blind hole recess 9 of the distal electrode 3, which was preferably drilled into the distal electrode 3.

In the exemplary embodiment shown, the center section 11 of the dumbbell-shaped element 1 has a round wire shape having a diameter in the millimeter range, for example, having a diameter of approximately 0.7 mm, and a length of several millimeters, for example a length in the range of approximately 5 mm to 8 mm.

The diameters of the spheres 6, 7 disposed at the two ends of the center section 11 are approximately 2 to 3 times greater than the diameter of the center section 11, wherein the respective diameter in a direction transversely to the longitudinal catheter axis (radial direction) is meant.

The first end section 7 of the dumbbell-shaped element 1 is positively anchored in the cylindrical blind hole recess 9 of the distal electrode 3. The second end section 6 serves as an axial stop for a loop 4 of the cable wire 2 which is wrapped around several times. The pull wire 2 is placed around the second end section 6 and looped around the same multiple times. As a result of the thickened region, the second end section 6 forms an axial stop for the loop 4. It is further preferred for the second end section 6 to comprise at least groove and, more preferably, two grooves 10, in which a respective steering cable 2 is disposed and guided back. The guidance of the pull wire ends in a bowline 5, which contracts at the pull wire 2 when a higher tensile load is applied. This connection yields considerably higher strength and dynamic resilience than conventional solutions.

The pull wire 2 is preferably formed of a braided section so as to achieve lower extensibility and a lower-friction surface. The diameter of the pull wire 2 is approximately 0.2 mm to 0.25 mm.

The dumbbell-shaped element 1 is preferably made of an NiTi alloy. The first end section 7 and the second end section 6 of the dumbbell-shaped element 1 can be generated, for example, by means of plasma jet melting from a wire section. For this purpose, the ends of the wire are melted inertly by means of a plasma jet (arc). As a result of the surface tension, the local melt forms spherules in the first end section 7 and the second end section 6. The method is extremely fast, reproducible and allows for high throughput.

The connection between the electrode 3 and the pull wire 2, shown in FIG. 1, is disposed at the distal end of the catheter 14, which is shown in FIG. 2. A catheter 14 according to the present invention further comprises, in this order in the proximal direction, an intermediate section 15, a catheter body 16, a steering handle 18, and a connection 19 for power, a signal, and/or media supply lines.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS

1 Dumbbell-shaped element
2 Pull wire
3 Distal electrode
4 Sheepshank
5 Bowline
6 Second end section of the dumbbell-shaped element 1
7 First end section of the dumbbell-shaped element 1
8 Solder
9 Blind hole recess
10 Groove
11 Center section of the dumbbell-shaped element 1
14 Catheter
15 Intermediate section
16 Catheter body
18 Steering handle
19 Connection for power, a signal and/or media supply lines

We claim:

1. A catheter comprising:
a steering cable anchor formed as an electrode, with the steering cable anchor disposed at a distal end of the catheter;
a steering cable; and
a substantially dumbbell-shaped element disposed between the steering cable anchor and the steering cable that connects the steering cable anchor to the steering cable,
wherein the dumbbell-shaped element comprises a first end section and a second end section and a center section interposed between them, wherein the first end section is connected to the steering cable anchor and the steering cable is attached to the second end section,
wherein the first end section and the second end section of the dumbbell-shaped element each have a maximum diameter in a radial direction of the dumbbell-shaped element, the maximum diameter of each of the first and second end sections being greater than a diameter of the center section in the radial direction of the dumbbell-shaped element, and
wherein a distal end of the steering cable is designed as a knot or loop which is wrapped around an outer surface of the center section of the dumbbell-shaped element such that the second end section forms an axial stop for the knot or loop over which the knot or loop cannot slide due to the diameter of the second end section being greater than the diameter of the center section, the knot or loop connecting the steering cable to the dumbbell-shaped element.

2. The catheter according to claim 1, wherein the steering cable contains a polymer.

3. The catheter according to claim 1, wherein the steering cable anchor and/or the dumbbell-shaped element contain a metallic material, wherein the dumbbell-shaped element is not ferromagnetic.

4. The catheter according to claim 1, wherein the first end section of the dumbbell-shaped element is connected substantially positively to the electrode.

5. The catheter according to claim 1, wherein the first end section and the second end section of the dumbbell-shaped element are designed as spheres, spherical segments, cones, conical segments or cylinders.

6. The catheter according to claim 1, wherein the distal end of the steering cable is designed as a loop which is wrapped around the second end section of the dumbbell-shaped element.

7. The catheter according to claim 1, wherein the maximum diameter of each of the first and second end sections is at least twice the size of the diameter of the center section in the radial direction of the dumbbell-shaped element.

8. The catheter according to claim 1, wherein the center section of the dumbbell-shaped element has a diameter of less than approximately 1 mm and a length of at least approximately 3 mm.

9. The catheter according to claim 8, wherein the center section of the dumbbell-shaped element has a length of at least approximately 5 mm.

10. The catheter according to claim 1, wherein the connection between the steering cable and the dumbbell-shaped element is effectuated without the use of adhesive.

* * * * *